Aug. 21, 1973 P. ECKE. JR Plant Pat. 3,394
POINSETTIA PLANT
Filed March 30, 1972
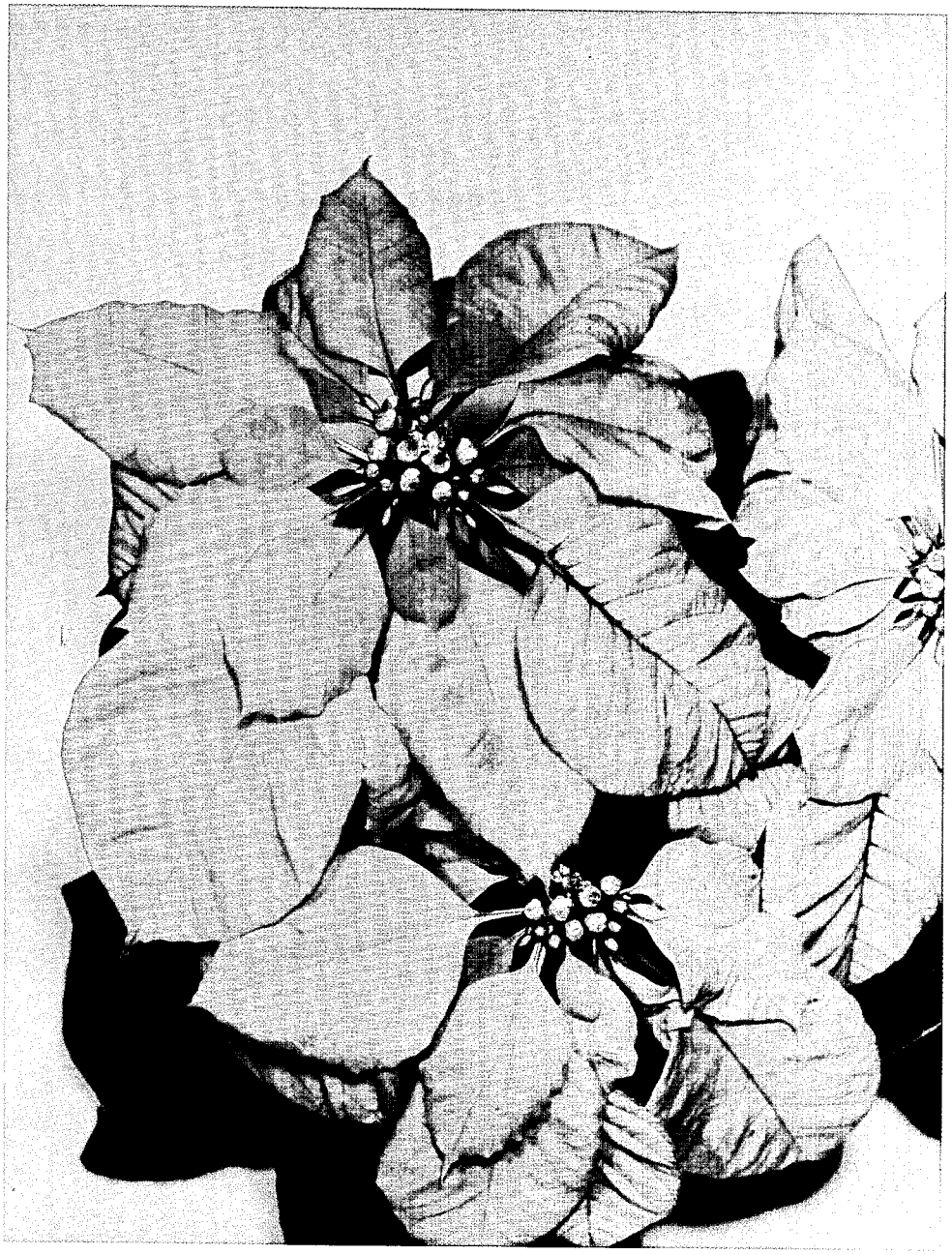

United States Patent Office

Plant Pat. 3,394
Patented Aug. 21, 1973

3,394
POINSETTIA PLANT

Paul Ecke, Jr., Encinitas, Calif., assignor to
Paul Ranch Ecke, Encinitas, Calif.

Filed Mar. 30, 1972, Ser. No. 239,833
Int. Cl. A01h 5/00
U.S. Cl. Plt.—86 1 Claim The present invention relates to a new and distinct variety of poinsettia plant, botanically known as *Euphorbia pulcherrima*, which was discovered by me as a cultivated tetraploid sport of the poinsettia variety known as "Annette Hegg" (Plant Pat. No. 2,962), said discovery having been made by me in one of my greenhouses located at Encinitas, Calif.

At the time of my discovery aforesaid, I was growing in my greenhouses at Encinitas various poinsettia varieties, including many plants of the patented variety "Annette Hegg." In the course of these growing operations, my atention was attracted to one particular plant among those of "Annette Hegg" which appeared to substantially differ from that variety in a number of prominent respects, including a shorter habit of growth, with thicker stems, larger, fleshier and darker green leaves, a more rounded bract form, and larger and more prominent cyathea. Close inspection of this particular plant showed that it had sported, so I carefully preserved the sport and kept it under close observation. In due course, I asexually reproduced the sport by vegetative cuttings taken therefrom and planted in my greenhouses at Encinitas. Continued observations of the original sport and its progeny derived from the vegetative cuttings aforesaid, fully confirmed that the aforementioned distinguishing features of this sport as originally recognized by me, among other differences subsequently noticed during continued observations, come true and remain stable. I am therefore convinced that the sport is a new and distinct poinsettia variety of good commercial value, as evidenced by the following unique combination of characteristics which are outstanding therein and which distinguishes it from all other varieties of which I am aware:

(1) A general resemblance to the variety known as "Annette Hegg" (Plant Pat. No. 2,962), but having a very short growth habit, with very thick stems;

(2) A uniform and fast rooting habit comparable to "Annette Hegg";

(3) Fewer stems and bracts than "Annette Hegg";

(4) Larger and fleshiesr leaves of a much darker green color than those of "Annette Hegg";

(5) A good bright red bract color, with some bluish tones;

(6) A more rounded bract form;

(7) Very large and more prominent cyathea; and (8) Long-lasting plant qualities.

The accompanying drawing shows a typical specimen plant of my new poinsettia variety as depicted in color as nearly true as it is reasonably possible to make the same in a color illustration of this character.

Although the details of my new poinsettia variety are generally similar in many respects to those described in Plant Pat. No. 2,962, to which reference may be readily had, the following brief description of the new sport is given for convenience, with color terminology in accordance with Wilson's Horticultural Colour Chart, except where general color terms of ordinary dictionary significance are obvious:

Parentage: Tetraploid sport of "Annette Hegg."

Propagation: Holds its distinguishing characteristics through succeeding propagations by vegetative cuttings.

Locality where grown and observed: Encinitas, Calif.

Form: Very short-growing, with very thick stems; compact.

Habit of growth: Self-branching, but does not produce as many stems or bracts as "Annette Hegg."

Rooting habit: Very uniform; very fast.

Blooming habit: Same as "Annette Hegg."

Blooming season: Same as "Annette Hegg."

Foliage: Larger and fleshier than "Annette Hegg," but otherwise similar in form. Color—Near Ivy Green, Plate 0001060/1; much darker in color than leaves of "Annette Hegg."

Bracts:

*Shape.*—More rounded than bracts of "Annette Hegg."

*Color.*—Good bright red, near Blood Red, Plate 820/3, with some bluish tones.

Flowers (Cyathea): Very large and prominent.

Reproductive organs:

*Stamens.*—Quite numerous. Color—Near Currant Red, Plate 821/2.

*Pollen.*—Color—Canary Yellow, Plate 2.

*Styles.*—Color—Near Blood Red, Plate 820.

*Ovaries.*—Color—Near Scheele's Green, Plate 860/1.

*Nectar cups.*—Color—Near Lemon Yellow, Plate 4/1.

General observations: While this new sport generally resembles its parent variety "Annette Hegg" in many respects, it particularly differs therefrom by having a shorter habit of growth, with thicker but fewer stems and produces fewer bracts; its leaves are larger, fleshier and much darker green in color; a more rounded bract form but having a good bright red color, with some bluish tones; and very large and prominent cyathea. The combination of these features is unique and makes my new variety a valuable addition to the line of red poinsettia varieties which have formerly been commercially available.

I claim:

1. A new and distinct variety of poinsettia plant, substantially as herein shown and described characterized particularly as to novelty by the unique combination of a general resemblance to the variety known as "Annette Hegg" (Plant Pat. No. 2,962), but having a very short growth habit, with very thick stems, a uniform and fast rooting habit comparable to "Annette Hegg," fewer stems and bracts than "Annette Hegg," larger and fleshier leaves of a much darker green color than those of "Annette Hegg," a good bright red bract color, with some bluish tones, a more rounded bract form, very large and more prominent cyathea, and long-lasting plant qualities.

No references cited.

ROBERT E. BAGWILL, Primary Examiner